United States Patent
Trieu

(10) Patent No.: US 8,979,901 B2
(45) Date of Patent: Mar. 17, 2015

(54) DYNAMIC BONE FASTENER WITH A PRESET RANGE OF MOTION

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 646 days.

(21) Appl. No.: 12/869,267

(22) Filed: Aug. 26, 2010

(65) Prior Publication Data

US 2012/0053640 A1 Mar. 1, 2012

(51) Int. Cl.
*A61B 17/70* (2006.01)
*A61B 17/86* (2006.01)

(52) U.S. Cl.
CPC .................. *A61B 17/7046* (2013.01)
USPC ........... 606/257; 606/264; 606/278; 606/308; 606/314; 606/331

(58) Field of Classification Search
USPC ......... 606/246–248, 254, 255, 257, 264–278, 606/282, 283, 286, 288, 305–308, 313, 314, 606/320, 331, 300, 301; 623/17.12, 17.13; 411/392, 424
See application file for complete search history.

(56) References Cited

U.S. PATENT DOCUMENTS

| | | | |
|---|---|---|---|
| 4,763,882 A * | 8/1988 | Nishiyama et al. | 267/33 |
| 5,415,661 A | 5/1995 | Holmes | |
| 6,267,764 B1 | 7/2001 | Elberg | |
| 2003/0191470 A1 | 10/2003 | Ritland | |
| 2005/0143737 A1 | 6/2005 | Pafford et al. | |
| 2005/0143823 A1 | 6/2005 | Boyd et al. | |
| 2005/0154390 A1* | 7/2005 | Biedermann et al. | 606/61 |
| 2008/0021465 A1* | 1/2008 | Shadduck et al. | 606/61 |
| 2008/0071273 A1 | 3/2008 | Hawkes et al. | |
| 2008/0161853 A1 | 7/2008 | Arnold et al. | |
| 2008/0161919 A1* | 7/2008 | Melkent | 623/17.11 |
| 2008/0306536 A1* | 12/2008 | Frigg et al. | 606/246 |
| 2009/0182380 A1 | 7/2009 | Abdelgany | |
| 2009/0264937 A1 | 10/2009 | Parrott | |
| 2010/0030279 A1 | 2/2010 | Flynn et al. | |
| 2010/0042157 A1 | 2/2010 | Trieu | |
| 2010/0057140 A1 | 3/2010 | Zucherman et al. | |
| 2010/0100137 A1 | 4/2010 | Justis et al. | |
| 2010/0168795 A1 | 7/2010 | Winslow et al. | |

OTHER PUBLICATIONS

U.S. Appl. No. 12/762,421, filed Apr. 19, 2010, titled "Load Sharing Bone Fastener and Methods of Use".
U.S. Appl. No. 12/394,362, filed Feb. 27, 2009, titled "Vertebral Rod System and Method of Use".

* cited by examiner

*Primary Examiner* — Michael T Schaper

(57) ABSTRACT

A bone fastener includes a fixation portion configured to interface with boney tissue, a connection portion having a longitudinal axis and being configured to interface with an elongated support structure, and a flexible portion disposed between the fixation portion and the connection portion. The flexible portion is configured to permit flexure of the connection portion relative to the fixation portion. The flexible portion has a first set of opposed facing surfaces that mechanically limit the range of flexure in a first direction. It has a second set of opposed facing surfaces that mechanically limit the range of flexure in a second direction. The opposed facing surfaces are substantially transverse to the longitudinal axis.

20 Claims, 14 Drawing Sheets

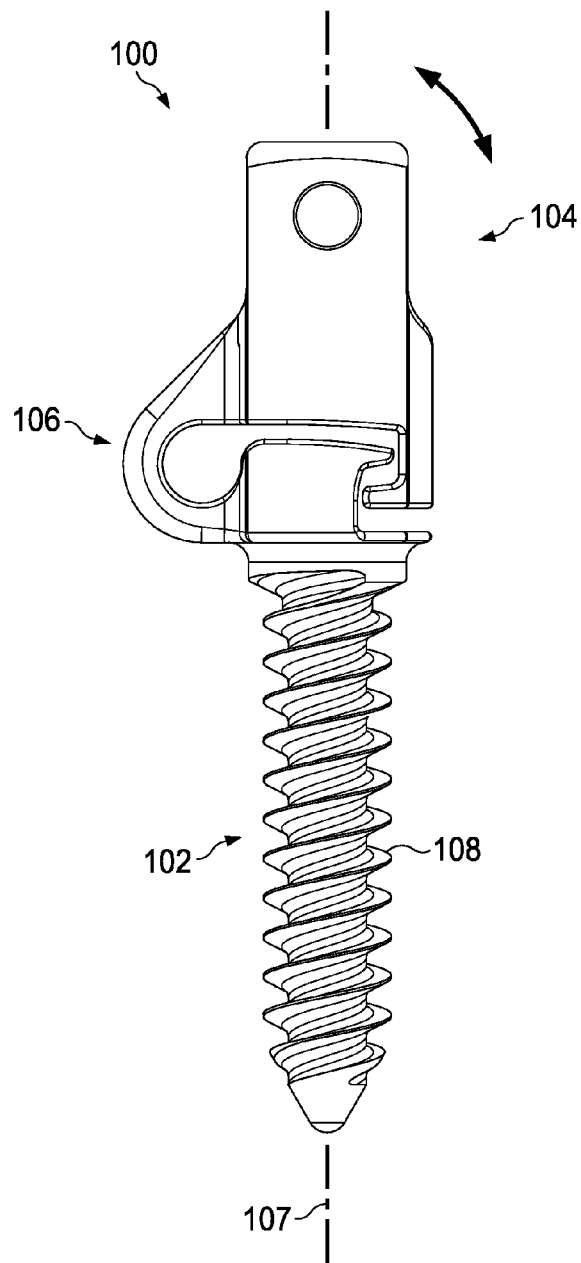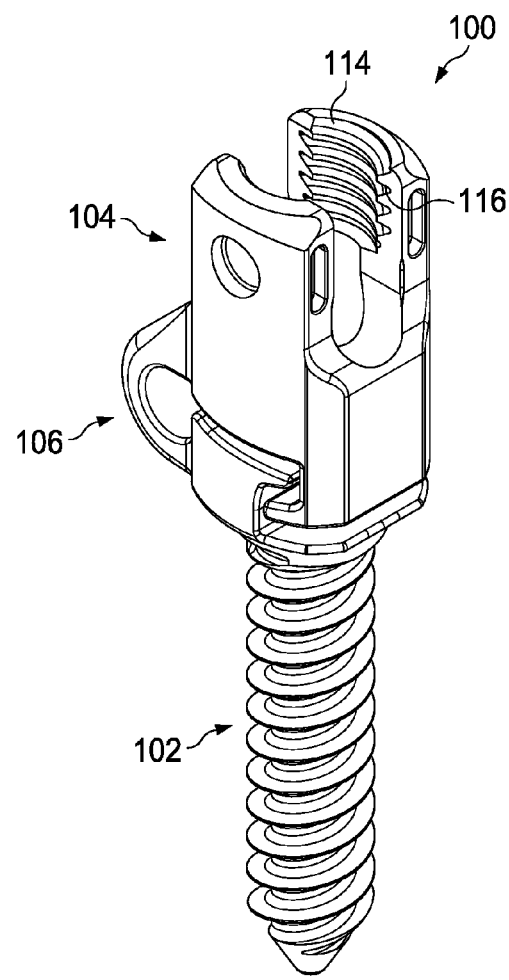
Fig. 1
Fig. 2

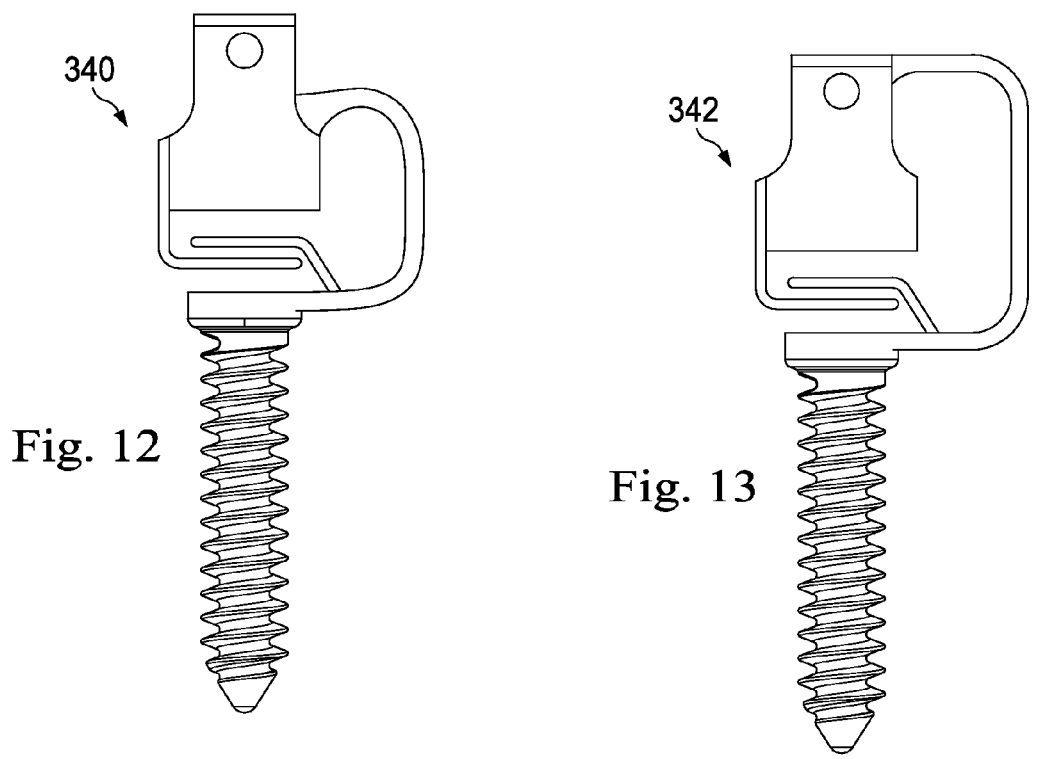

DYNAMIC BONE FASTENER WITH A PRESET RANGE OF MOTION

FIELD OF THE INVENTION

The present disclosure is directed to dynamic bone fasteners, and more particularly, to dynamic type bone fasteners having a preset range of motion.

BACKGROUND

Several techniques, systems, and supporting structures have been developed for correcting and stabilizing the spine. Some systems use supporting structures like a rod, a tether, a ligament, or others disposed longitudinally along a length of the spine or vertebral column. In accordance with such a system, the supporting structure is engaged to various vertebrae along a length of the spinal column by way of a number of fixation elements. A variety of fixation elements are configured to engage specific portions of the vertebra. For instance, one such fixation element is a hook that is configured to engage the laminae of the vertebra. Another very prevalent fixation element is a spinal bone screw which can be threaded into various aspects of the vertebral bone or pelvis. For example, a plurality of spinal bone screws can be threaded into a portion of several vertebral bodies and the sacrum, such as, for example, the pedicles of these vertebrae. The supporting structures can then be affixed to these spinal bone screws to apply corrective and stabilizing forces to the spine.

Because conventional rods and screw are rigid, relatively high levels of stresses and strain can be introduced to the supporting bone structure during cyclic loading that occurs during a patient's normal activities. Conventional fixation elements can be improved to more easily accommodate the loads, while reducing the introduction of stress into the boney support tissue.

The devices and systems disclosed herein overcome one or more of the shortcomings of prior art devices.

SUMMARY

In one exemplary aspect, the present disclosure is directed to a bone fastener configured to penetrate into boney tissue and connect with an elongated support structure. The bone fastener includes a fixation portion configured to interface with boney tissue, the fixation portion having a longitudinal axis, a connection portion configured to interface with an elongated support structure, and a flexible portion disposed between the fixation portion and the connection portion. The flexible portion is configured to permit flexure of the connection portion relative to the fixation portion. The flexible portion has a first set of opposed facing surfaces that mechanically limit the range of flexure in a first direction. It has a second set of opposed facing surfaces that mechanically limit the range of flexure in a second direction. The opposed facing surfaces are substantially transverse to the longitudinal axis.

In one aspect, a dampening material is disposed between the first set of opposed facing surfaces and disposed between the second set of opposed facing surfaces. In one aspect, the dampening material is disposed to fill only a portion of the area between the first set of opposed facing surfaces and to fill only a portion of the area between the second set of opposed facing surfaces.

In another exemplary aspect, the present disclosure is directed to a bone fastener configured to penetrate into boney tissue and connect with an elongated support structure. The bone fastener includes a longitudinal axis and a fixation portion configured to interface with boney tissue, a connection portion configured to interface with an elongated support structure, and a flexible portion disposed between the fixation portion and the connection portion. The flexible portion is configured to permit flexure of the connection portion relative to the fixation portion. The flexible portion includes an upper portion merging with the connection portion and a lower portion merging with the fixation portion. It also includes a connecting portion extending from the upper portion to the lower portion, where the connecting portion is configured to flex to displace the upper portion relative to the lower portion. The flexible portion also includes a motion limiter portion that comprises a first set of opposed facing surfaces that mechanically limits the range of flexure in a first direction. A first distance between the first set of opposed facing surfaces forms a first gap region. The motion limiter portion also includes a second set of opposed facing surfaces that mechanically limits the range of flexure in a second direction. A second distance between the second set of opposed facing surfaces forms a second gap region. The opposed facing surfaces are substantially transverse to the longitudinal axis.

In another exemplary aspect, the present disclosure is directed to a system for stabilization of boney structure. It includes an elongated support structure and at least two bone fasteners configured to penetrate into boney tissue and connect with the elongated support structure. Each bone fastener includes a longitudinal axis and a fixation portion configured to interface with boney tissue, a connection portion configured to interface with the elongated support structure, and a flexible portion disposed between the fixation portion and the connection portion. The flexible portion is configured to permit flexure of the connection portion relative to the fixation portion. The flexible portion has a first set of opposed facing surfaces that mechanically limit the range of flexure in a first direction. It has a second set of opposed facing surfaces that mechanically limit the range of flexure in a second direction. The opposed facing surfaces are substantially transverse to the longitudinal axis.

Further aspects, forms, embodiments, objects, features, benefits, and advantages of the present invention shall become apparent from the detailed drawings and descriptions provided herein.

BRIEF DESCRIPTION OF THE DRAWINGS

The accompanying drawings serve to exemplify some of the embodiments of this invention.

FIGS. 1-4 are illustrations of an exemplary dynamic bone fastener for securing an elongated support structure in accordance with one or more aspects of the present disclosure.

FIGS. 12-14 are illustrations of other exemplary dynamic bone fasteners for securing an elongated support structure in accordance with one or more aspects of the present disclosure.

DETAILED DESCRIPTION

Figure 3:
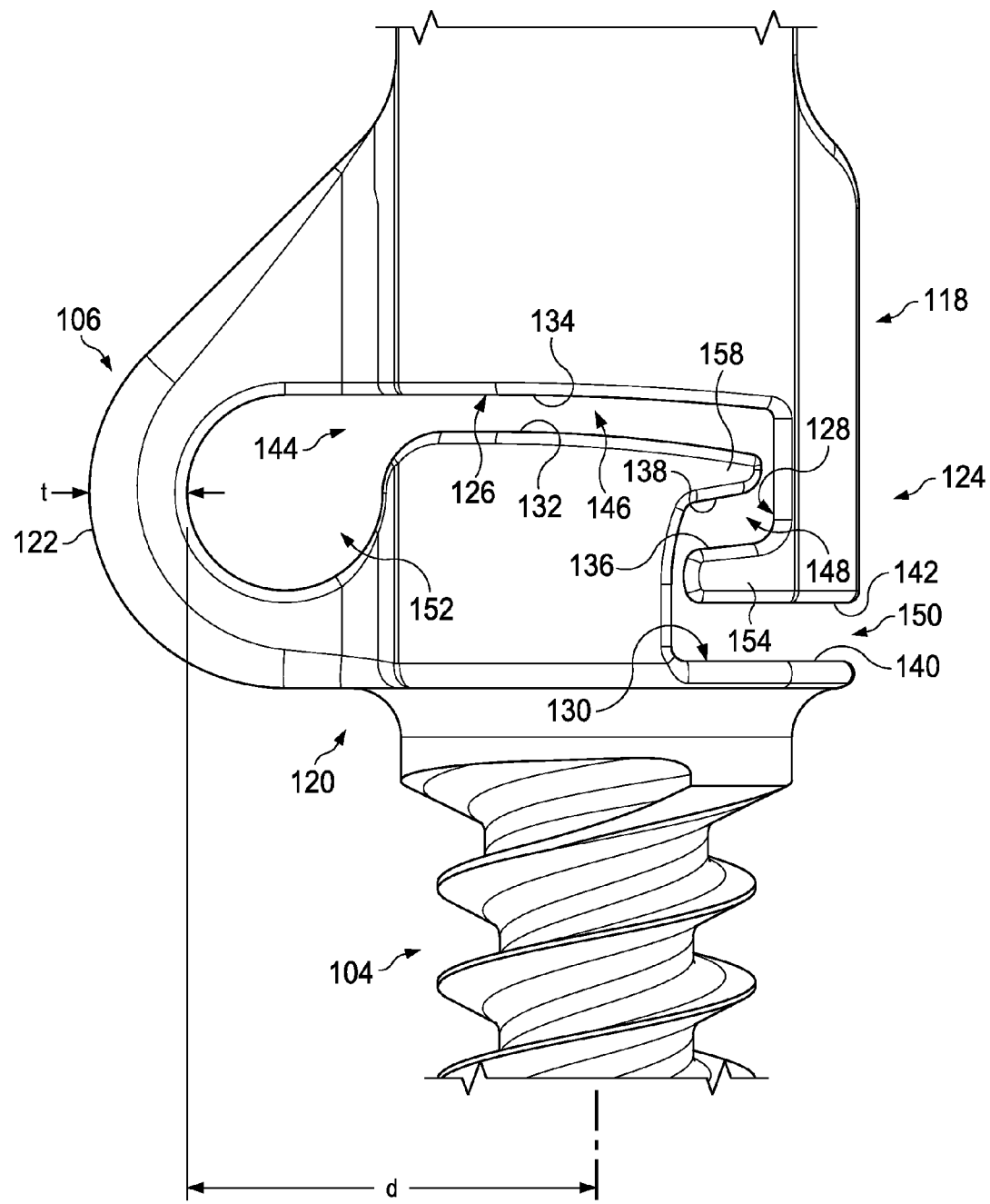

The present disclosure relates generally to the field of implantable bone fasteners, and more particularly to dynamic bone fasteners and systems for implantation in a patient during a surgical procedure to provide stabilizing support to bone structure and tissue. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

The flexible bone fasteners disclosed herein are configured to provide stabilization to patient tissue, while at the same time reducing stresses by having a dynamic features that are limited in their range of motion to a preestablished therapeutic range of rotation. In addition, some embodiments control the articulation to permit greater articulation in one of flexion or extension than the other. The fasteners may be used in cooperation with, for example, an elongated support structure. It is envisioned that employment of the bone fasteners with an elongated support structure provides stability and maintains structural integrity while reducing stress on spinal elements. The flexible bone fasteners may also be used with other constructs such as plates. It is contemplated that a bone construct may include the bone fastener only, in for example fracture repair applications.

The devices and embodiments in the present disclosure may be employed to treat spinal disorders such as, for example, degenerative disc disease, disc herniation, osteoporosis, spondylolisthesis, stenosis, scoliosis and other curvature abnormalities, kyphosis, tumors, and fractures, among other disorders. It is envisioned that the fasteners of the present disclosure may be employed with surgical treatments including open surgery and minimally invasive procedures, such as, for example, discectomy, laminectomy, fusion, bone graft, implantable prosthetics and/or dynamic stabilization applications. It is contemplated that the present disclosure may be employed with other osteal and bone related applications, including those associated with diagnostics and therapeutics. It is further contemplated that the disclosed bone fasteners may be employed in a surgical treatment with a patient in a prone or supine position, employing a posterior, lateral, or anterior approach. The present disclosure may be employed with procedures for treating the lumbar, cervical, thoracic and pelvic regions of a spinal column.

Various embodiments are described as being used with elongated support structures, such as a ligament, a tether, or a rod. However, these embodiments are not limited to being used with the specific type of elongated support structures described. It is contemplated that any of the embodiments described herein may be used with any elongated support structure, including but not limited to ligaments, rods, tethers, bands, rigid, semi-rigid, flexible, dynamic, metal polymer PEEK, composites, and natural or synthetic devices, known and unknown. In addition, these embodiments are described as being connected to anchor portions that are shown as threaded anchors. It is contemplated that hooks or other bone connecting mechanisms can be used in place of the threaded anchors.

FIGS. 1-4 show one embodiment of an exemplary bone fastener 100. The bone fastener 100 comprises a fixation portion 102, a connection portion 104, and a flexible portion 106. A longitudinal axis 107 through the fastener 100 is shown for reference. The fixation portion 102 is configured to interface or engage with bone structure to secure the bone fastener in place. In the embodiment shown, the fixation portion 102 is a bone screw having outwardly extending threads 108 configure to penetrate boney tissue. However, in other embodiments, the fixation portion is a hook, clamp, or other structure configured to interface or engage the bone structure.

Figure 4:
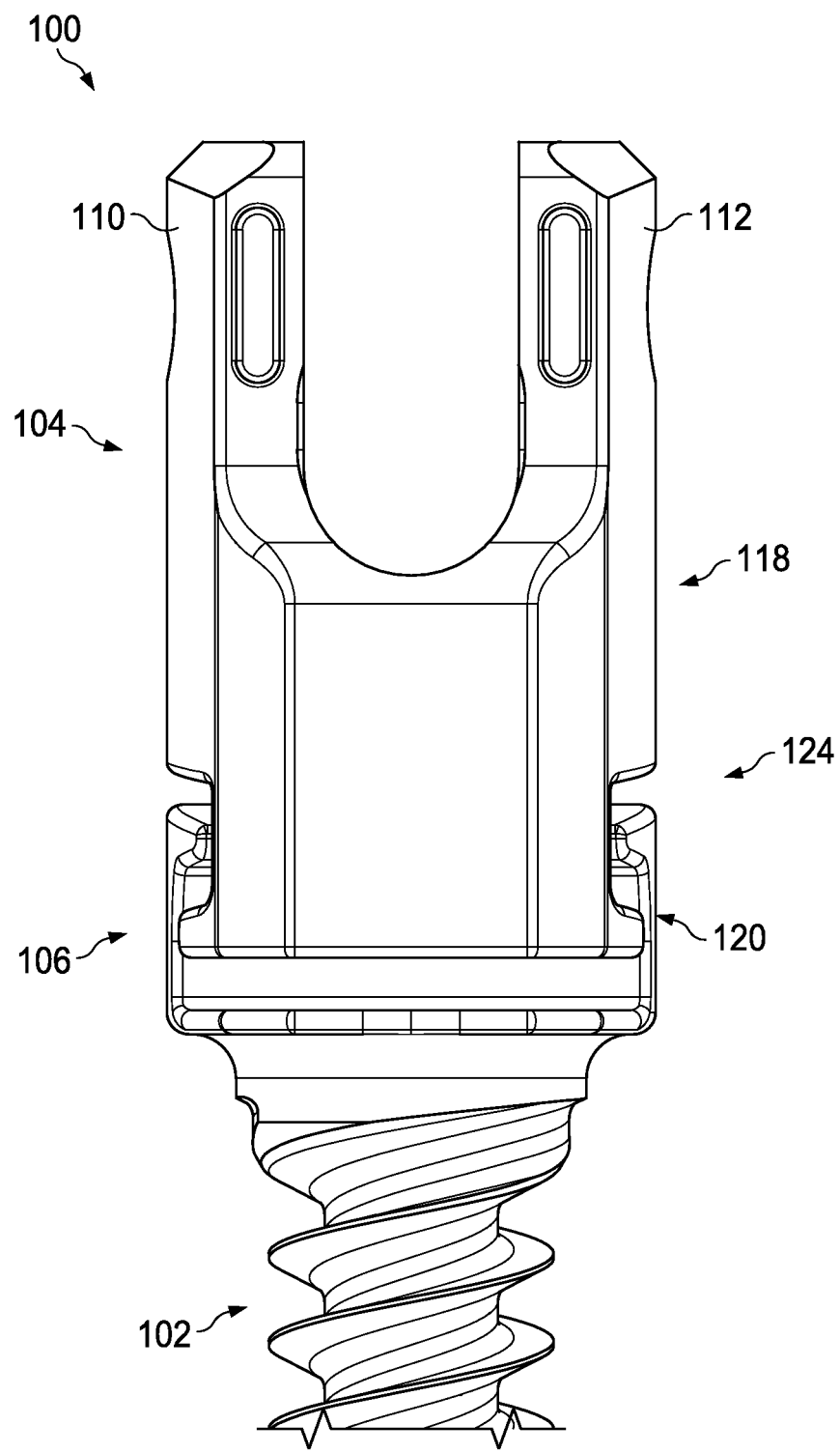

The connection portion 104 is configured to engage an elongated support structure. In this embodiment, the connection portion 104 is a U-shaped receiver comprising a first arm 110 and a second arm 112 (as best seen in FIG. 4), spaced to receive an elongated support structure, like a ligament. The receiver includes an inner surface 114 with threads 116 formed therein (best seen in FIG. 2) configured to threadably receive a set screw to secure the elongated support structure in the receiver. Although shown as a U-shaped receiver, other embodiments of the connection portion 104 include a bores or through holes, clamps, and other systems and arrangements for receiving an elongated support structure.

The flexible portion 106 enables dynamic movement between the fixation portion 102 and the connection portion 104, as indicated by the directional arrows in FIG. 1. It is configured to allow the connection portion 104 to pivot within a preestablished range in both a rearward and forward direction. It provides stability and structural integrity while reducing stress on spinal elements, the bone tissue engaged with the fixation portion 102, the supporting structure 104, or any elongated structure attached thereto. As described further below, the bone fastener with an elongated support structure provides displacement limits that may restrict bone fastener articulation to a therapeutic range by establishing limits on the degree of articulation.

In this embodiment, the flexible portion 106 is formed integrally with the fixation portion 102 and the connection portion 104. Accordingly the flexible portion 106 and the connection portion 104 are a single unitary body. Here, the flexible portion 106 flexes as a result of elastic deformation. As will be described below however, some embodiments are multi-axial-type fasteners that include additional articulation between the fixation portion 102 and the connection portion 104. In this embodiment, the flexible portion 106 is arranged to flex about a point offset from the longitudinal axis 107 of the fastener 100.

The flexible portion 106 will be described primarily with reference to FIG. 3. In this embodiment, the flexible portion 106 includes an upper portion 118, a lower portion 120, a connecting portion 122 extending from the upper portion 118 to the lower portion 120, and a motion limiter portion 124. The upper portion 108 may form the lower surface of the lower portion of the connection portion 104. In the embodiment in FIGS. 1-4, where the bone fastener 100 is a monoaxial screw, the lower portion 120 of the flexible portion 106 may form an upper portion of the fixation portion 104. The connecting portion 122 connects the upper and lower portions 118, 120 at a location offset from the longitudinal axis 107. It is the flexure of the connecting portion 122 that provides the bone fastener 100 with its dynamic nature or its movement capability. As such, as the connecting portion 122 flexes, such as by elastic deformation, so that the upper portion 118 can move or displace relative to the lower portion 120 as indicated by the two arrows in FIG. 1. In the embodiments shown, the connecting portion 122 is constrained to provide directional displacement. For example, if flexes more in an up and down direction (or flexion and extension direction), but less in a lateral direction. In some embodiments, the motion occurs substantially in a single plane. In should be noted that in other embodiments, the connecting portion is a hinge and achieves movement between the upper and lower portions 118, 120 not through elastic deformation, but through articulation about a pivot point.

The motion limiter portion 124 limits the range of motion or articulation obtainable by the flexible portion 106 in both the upper and lower directions. Here, the motion limiter portion 124 includes a plurality of surfaces that interface through contact or mechanical interference to limit the distance that the upper portion 118 can travel relative to the lower portion 120 in either an upward or downward direction. Particularly, in this embodiment, the motion limiter portion 124 includes a first set of opposed facing surfaces 126, a second set of opposed facing surfaces 128, and a third set of opposed facing surfaces 130. The first set includes a first lower mechanical stop surface 132 and a first upper mechanical stop surface 134. The second set includes a second lower mechanical stop surface 136 and a second upper mechanical stop surface 138. The third set includes a third lower mechanical stop surface 140 and a third upper mechanical stop surface 142.

A gap 144 extends between each of the mechanical stop surfaces of the first, second, and third sets of surfaces 126, 128, 130, and is defined by three regions, each region being formed between one of the respective sets of surfaces. Accordingly, the gap 144 includes a first gap region 146 disposed between the first set of opposed facing surfaces 126, a second gap region 148 disposed between the second set of opposed facing surfaces 128, and a third gap region 150 disposed between the third set of opposed facing surfaces 130. A fourth gap region 152 is formed by the shape of the connecting portion 122 and provides a space for the displacement of the connecting portion 122.

In the embodiment shown, the motion limiter portion 124 includes an inwardly projecting tab 154 that includes the second lower mechanical stop surface 136 and the third upper mechanical stop surface 142. In this exemplary embodiment, the tab 154 extends from an arm 156 connected to the upper portion 118. The tab 154 extends in a direction relatively transverse to the longitudinal axis 107.

A catch 158 disposed directly vertically above or below the tab 154 includes the first lower mechanical stop surface 132 and the second upper mechanical stop surface 138. In this arrangement, the second upper mechanical stop surface 138 is located to contact the second lower mechanical stop surface 136 on the tab 154 as the tab moves about the connection portion 122, mechanically stopping the movement of the tab 154. More particularly, the second lower mechanical stop surface 136 mechanically interfaces with the second upper mechanical stop surface 138 to limit upward movement of the upper portion 118.

In addition, in the exemplary embodiment shown, the third upper mechanical stop surface 142 mechanically interfaces with the third lower mechanical stop surface 140 to limit downward movement of the upper portion 118. The distance between the second lower and upper mechanical stop surfaces 136, 138, and the distance between the third lower and upper mechanical stop surfaces 140, 142 dictates the range of motion achieved by the bone fastener 100 and maintains the range of motion within therapeutic levels.

It should be noted that in the embodiment described with reference to FIGS. 1-4, other arrangements may be used to limit the range of motion achieved by the fastener 100. For example, in one embodiment, instead of using the third lower and upper mechanical stop surfaces 140, 142 to limit the downward motion of the upper portion 118, the first lower and upper mechanical stop surfaces 132, 134 may be used to limit the downward motion of the upper portion 118. In other embodiments, both the first lower and upper mechanical stop surfaces 132, 134 and the third lower and upper mechanical stop surfaces 140, 142 simultaneously limit the range of motion of the upper portion 118 by acting as a mechanical stop.

The embodiment in FIG. 3 shows the flexible portion 106 in a neutral or unloaded condition. In this condition, the upper portion has the ability to move either in the upward or downward direction. The structural make-up of the flexible portion 106, including the connecting portion 122, biases the flexible portion 106 to the neutral or unloaded condition.

The stiffness of the flexible portion 106 can be controlled by selection of the material and by the dimensions of the connecting portion 122. Particularly, by controlling the thickness t of the connecting portion 122, the width (not shown) of the connecting portion 122, and the distance d of the connecting portion from the longitudinal axis 107, the flexible portion 106 can be designed to provide the desired stiffness. Here, the connecting portion 122 has a thickness t. It is envisioned that thickness t of the connecting portion may be in a range of 1-10 mm, preferably in a range of 2-6 mm, and most preferably in a range of 2-4 mm. The distance to the inner surface of the connecting portion 122 is defined as an offset distance d measured from the longitudinal axis 107. It is envisioned that the offset distance d may be in a range of 2-20 millimeters (mm), preferably in a range of 2-15 mm, and most preferably in a range of 2-10 mm. In the embodiment shown, the connecting portion 122 has a width that is less than the width of the upper and lower portions 118, 120 of the flexible portion 106, as can be understood by FIG. 4. However, in some embodiments, the width of the connecting portion may be larger or smaller and may be selected during manufacturing to provide a desired resistance to motion. In some examples, the width of the connecting portion may be in a range of 3-20 mm, preferably in a range of 3-15 mm, and most preferably in a range of 3-10 mm. It is further envisioned that cross-sectional of the connecting portion 122 can be uniform, non-uniform, consistent or variable. It is contemplated that the connecting portion 122 may have alternate geometric cross-section configurations, for example, round, oval, rectangular, polygonal, irregular, uniform and non-uniform and have a corresponding cross-sectional area based on the particular geometry.

In one embodiment, thickness t of the connecting portion is less than half the offset distance d to provide greater flexibility to the bone fastener. In another embodiment, the width w of the connecting portion is less than half the width of the connecting portion 104 to provide greater flexibility to the bone fastener 100.

The below paragraphs describe many bone fastener features usable on the bone fastener 100 and describe some alternative embodiments. Since there are many similarities between the bone fastener 100 and the bone fasteners described below, the discussion of the bone fasteners below will be limited to the portions unique to those features or embodiment.

Figure 5:
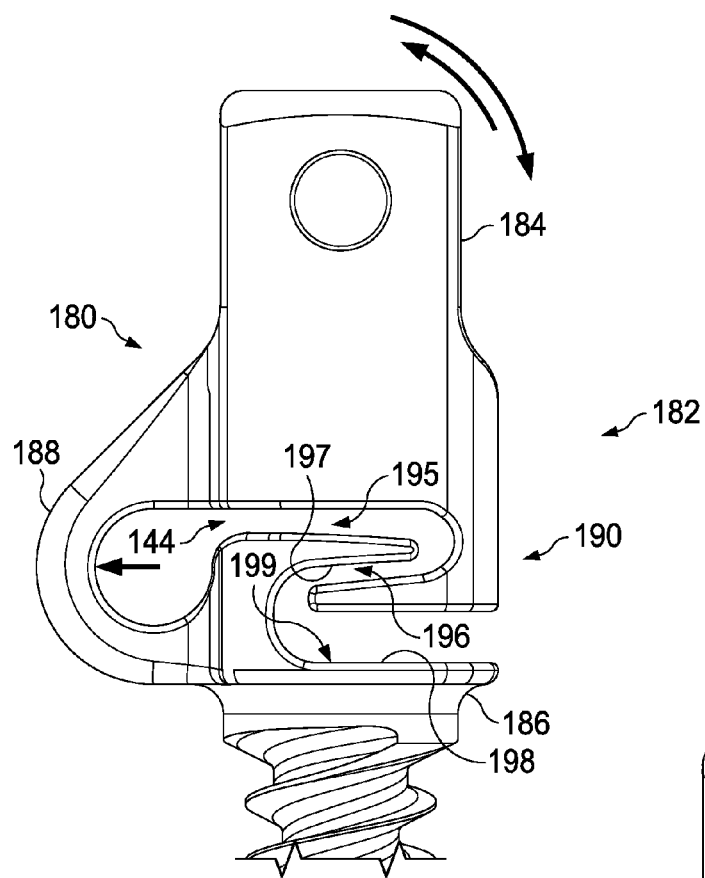
FIG. 5 is an illustration of another exemplary dynamic bone fastener for securing an elongated support structure in accordance with one or more aspects of the present disclosure.

FIG. 5 shows another embodiment of a bone fastener, referenced herein by the reference numeral 180. Like the bone fastener 100 discussed above, the bone fastener 180 has a flexible portion 182 that includes an upper portion 184, a lower portion 186, a connecting portion 188, and a motion limiter portion 190. The motion limiter portion 190 includes a gap 192 with a first gap region 194 disposed between a first set of opposed facing surfaces 195, a second gap region 196 disposed between the second set of opposed facing surfaces 197, and a third gap region 198 disposed between the third set of opposed facing surfaces 199. As can be seen in FIG. 5, unlike the gaps in FIG. 3 that were substantially the same distance, the gap distances in FIG. 5 are uneven.

In the example shown in FIG. 5, the gap size in the second gap region 196 is substantially smaller than the gap size of the first or third gap regions 194, 198. Accordingly, the range of upward motion is less than the range of downward motion as indicated by the direction arrows in FIG. 5. Accordingly, the second set of mechanical stop surfaces 197 limit the upward rotation before either of the first or third sets of mechanical stop surfaces 195, 199. The gap sizes are measured when the flexible portion 182 is at the neutral or unbiased position.

Figure 6A:
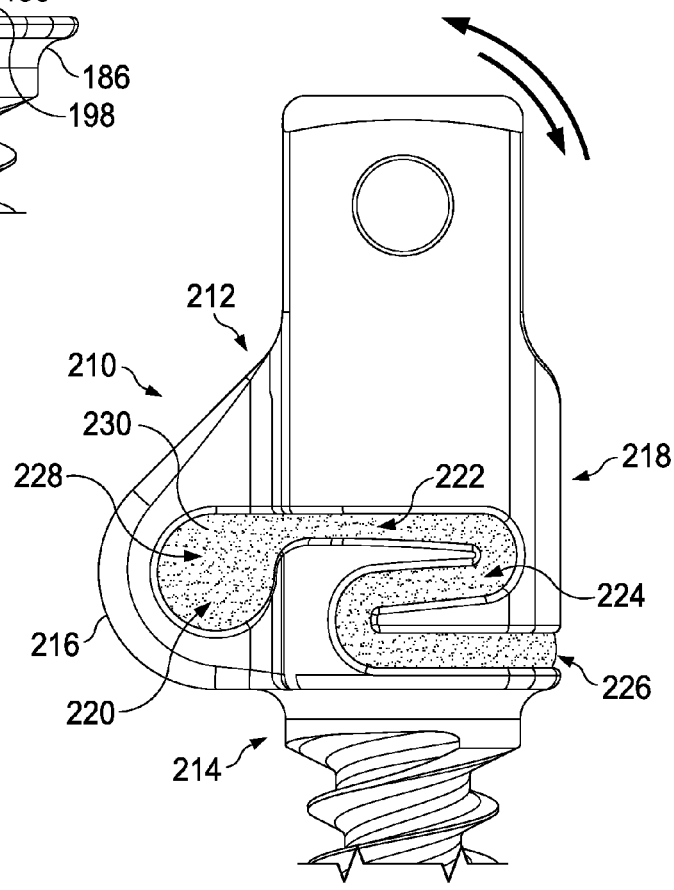
FIG. 6A is an illustration of another exemplary dynamic bone fastener for securing an elongated support structure in accordance with one or more aspects of the present disclosure.

FIG. 6A discloses another embodiment of a bone fastener 210. Like the embodiments discussed above, the bone fastener 210 includes an upper portion 212, a lower portion 214, a connecting portion 216, and a motion limiter portion 218. As in other embodiments, the upper and lower portions 212, 214 are separated by a gap 220 forming a part of the motion limiter 218. The gap 220 includes a first gap region 222 disposed between a first set of opposed facing surfaces, a second gap region 224 disposed between the second set of opposed facing surfaces, and a third gap region 226 disposed between the third set of opposed facing surfaces. The gap 220 also includes a fourth gap region 228 formed by the shape of the connecting portion 216.

In this case, each of the gap regions 222, 224, 226 is filled with a dampening material 230 that provides elastic or resilient dampening. The material 230 may be, for example, polyurethane, among others. Since the gap regions 222, 224, 226 are filled with dampening material, the associated mechanical stop surfaces of the sets of opposed facing surfaces do not provide an abrupt end of motion. Instead, resistance to motion increases as the displacement increases and as the dampening material becomes more compacted between surfaces. In the embodiments shown in FIG. 6A, the whole gap 220 is filled to maximize the motion dampening. As such, the dampening material in first and third gap regions 222, 226 provide resistance to downward movement, and the dampening material in second gap region 224 provides resistance to upward movement. Therefore, the dampening is unequally distributed to provide a desired dampening effect. It is worth noting that because of the dampening material between opposed facing surfaces, the mechanical stop surfaces do not contact each other to provide the stop limits. Instead, they compact the dampening material. Even still, the surfaces mechanically limit the range of motion because they support the intervening dampening material.

The dampening material 230 may be selected of any compressible material to achieve a desired resistance or to modulate the resistance to motion. It may have any modulus or hardness, may be solid or porous, and may be formed of a single or multiple material. In some embodiments, the dampening material fills only a part of the gap in each gap region. In addition, the material may be a permanent or resorbable material. In one example, the dampening material is drug eluting. In some embodiments, the dampening material may be more resistance to motion in flexion than extension, or vice versa.

Figure 6B:
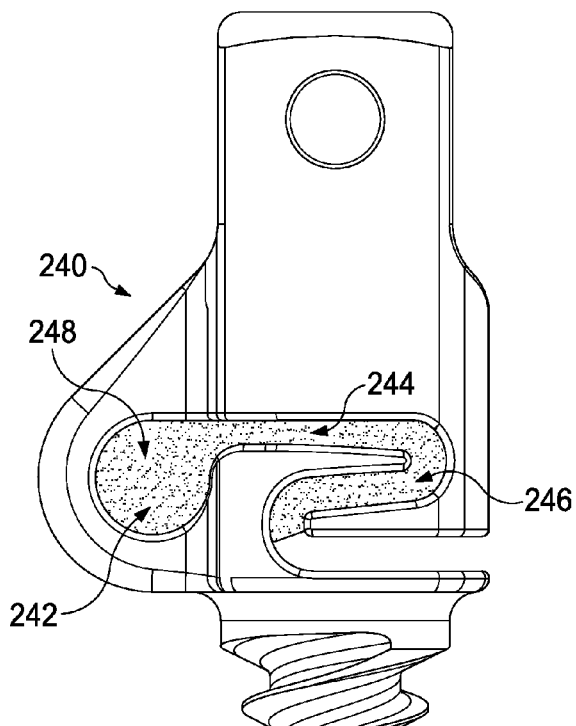
FIG. 6B is an illustration of another exemplary dynamic bone fastener for securing an elongated support structure in accordance with one or more aspects of the present disclosure.

FIG. 6B shows a bone fastener 240 with a different dampening configuration. This embodiment includes a dampening material 242 disposed in only a first, a second, and a fourth gap region, referenced as 244, 246, and 248. Accordingly to this embodiment, the dampening material 242 in the first region 244 resists downward motion and the dampening material 242 in the second region 246 resists upward motion. In this manner the dampening resistance may be configured to be equal or substantially equal in both upward and downward motion.

Figure 6C:
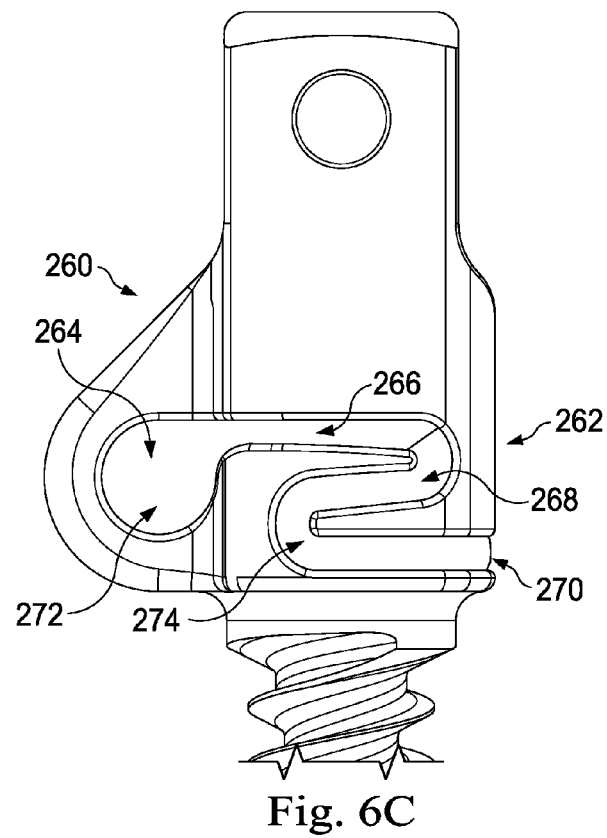
FIG. 6C is an illustration of another exemplary dynamic bone fastener for securing an elongated support structure in accordance with one or more aspects of the present disclosure.

FIG. 6C shows a bone fastener 260 having a flexible portion 262 with a gap 264 including first, second, third, and fourth gap regions, referenced as 266, 268, 270, 272, respectively. Here, a dampening material 274 is disposed only in the second and third regions 268, 270. Accordingly, the dampening material 274 in the second region 268 resists upward motion and the material 274 in the third region 270 resists downward motion.

Some embodiments use dampening materials with different characteristics in different regions. For example, in one embodiment, the dampening material in the second region is a first material and the material in the third region is a second dampening material different than the first material, and having a different compressive characteristic. In such a manner, the fastener may be manufactured to achieve any desired compressive profile.

Consistent with the description above, dampening material can be inserted or used to fill one or more of the gaps to modulate the stiffness or flexibility. The dampening materials can be of various modulus or hardness, solid or porous, inert or bioactive (e.g. controlled release of biological or pharmacological agents, etc.). In some examples, the dampening material itself may function as a drug-eluting implant. In one embodiment of the present invention, the dampening material is molded using standard mold technology so as to produce a pre-molded implant from a drug-eluting biocompatible matrix containing at least one elutable drug or therapeutic agent. The dampening material can be made to fit into one or more gaps within the flexible portion of the bone fastener. The drug-eluting dampening material of the present invention may be made from an elastomeric material suitable for both mechanical dampening and drug elution. The drug or therapeutic agent can be selected from the group consisting of analgesic compounds, anesthetics, antibacterial compounds, antibiotics, antibodies, antifungal compounds, anti-inflammatories, antiparasitic compounds, antiviral compounds, anticancer compounds, carbohydrates, cells, cytokines, drugs, genetic agents, enzyme inhibitors, hormones, steroids, glucocorticosteroids, growth factors, immunoglobulins, immunomodulators, lipoproteins, minerals, neuroleptics, nutritional supplements, oligonucleotides, organic polymers, peptides, polysaccharides, proteins, proteoglycans, radiocontrast media, toxins, tumoricidal compounds, tumorstatic compounds, and vitamins.

Figure 7:
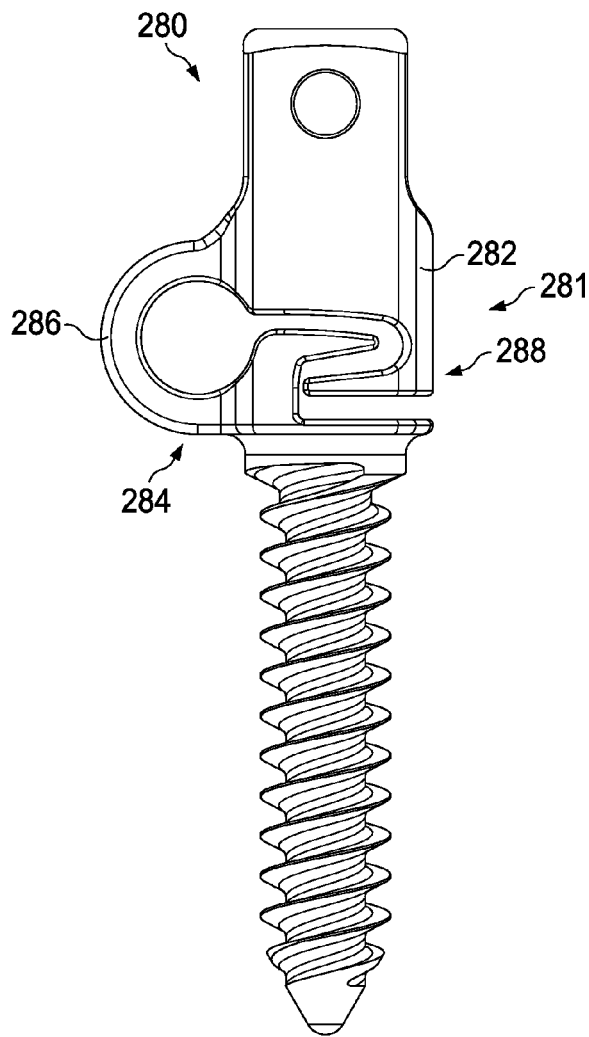
FIGS. 7 and 8 are illustrations of other exemplary dynamic bone fasteners for securing an elongated support structure in accordance with one or more aspects of the present disclosure.

FIG. 7 shows another embodiment of a bone fastener referenced by the numeral 280, including a flexible portion 281 with an upper portion 282, a lower portion 284, a connecting portion 286, and a motion limiter portion 288. Here, the connecting portion 286 is formed in a more "round" and evenly distributed manner, with a larger inner radius in an attempt to improve flexibility, stress distribution, and durability, than the connecting portion 122 in FIGS. 1-4. In addition, flexible portion includes gaps that are larger than those in the embodiment shown in FIGS. 1-4. These gaps provide a larger range of motion (ROM).

Figure 8:
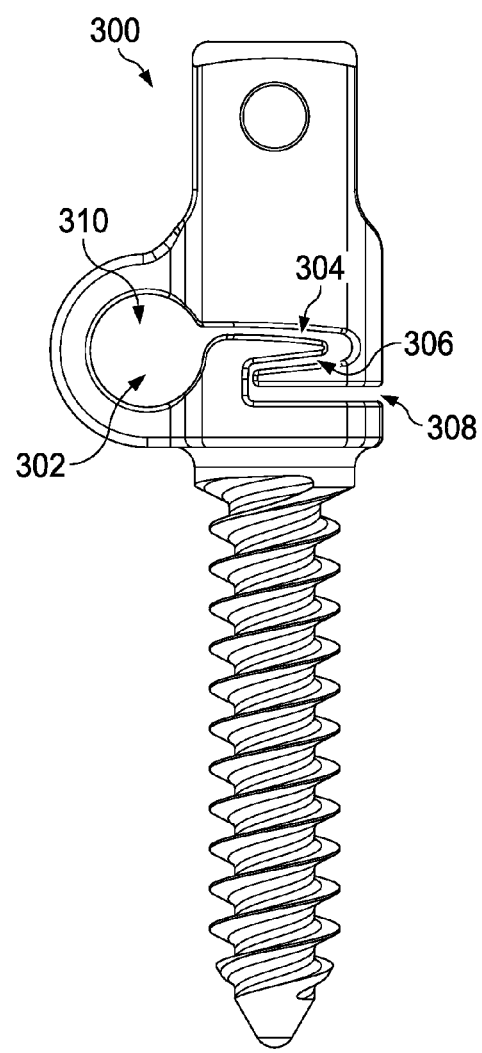

FIG. 8 shows another embodiment of a bone fastener, referenced by the numeral 300. Compared to the fastener 280 in FIG. 7, the fastener 300 in FIG. 8 includes smaller gaps to provide a more limited ROM. Particularly, the fastener includes a gap 302 formed of a first gap region 304 disposed between a first set of opposed facing surfaces, a second gap region 306 disposed between the second set of opposed facing surfaces, a third gap region 308 disposed between the third set of opposed facing surfaces, and a fourth gap region 310. Here, the first gap region 304 that defines the range of flexion is slightly larger than second gap region 306 that defines the range of extension in order to allow more flexion than extension. Similar effects can be achieved by putting a harder dampening material in the second gap region 306 for more resistance to extension.

Figure 9A:
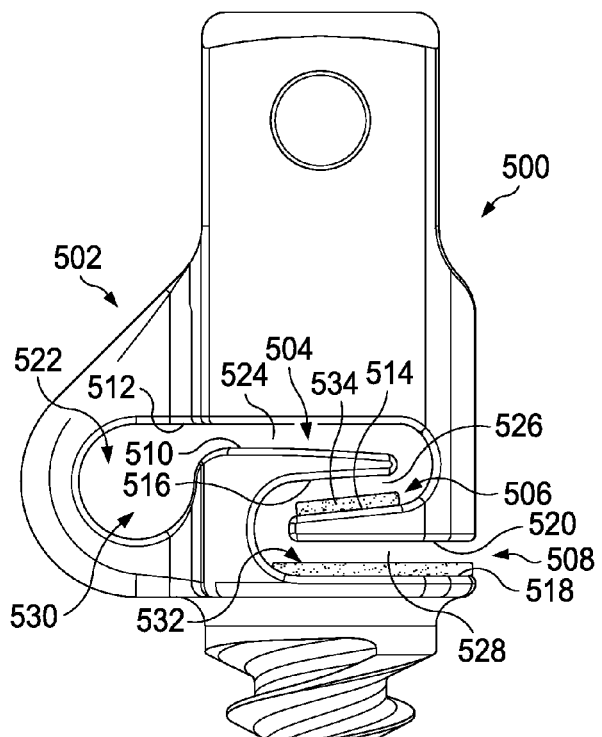
FIG. 9A is an illustration of another exemplary dynamic bone fastener for securing an elongated support structure in accordance with one or more aspects of the present disclosure.

FIG. 9A shows another embodiment of a bone fastener, referenced by the numeral 500. In many ways, the fastener 500 is similar to the fastener 280 in FIG. 7. One difference between the fasteners is that the fastener 500 includes dampening material in its gap. Like the fasteners described above, and referring to FIG. 9A, the bone fastener 500 includes a motion limiter portion 502 including a first set of opposed facing surfaces 504, a second set of opposed facing surfaces 506, and a third set of opposed facing surfaces 508. The first set 504 includes a first lower mechanical stop surface 510 and a first upper mechanical stop surface 512. The second set 506 includes a second lower mechanical stop surface 514 and a second upper mechanical stop surface 516. The third set 508 includes a third lower mechanical stop surface 518 and a third upper mechanical stop surface 520.

A gap 522 extends between each of the mechanical stop surfaces of the first, second, and third sets of surfaces 504, 506, 508, and is defined by three regions, each region being formed between one of the respective sets of surfaces. Accordingly, the gap 522 includes a first gap region 524 disposed between the first set of opposed facing surfaces 504, a second gap region 526 disposed between the second set of opposed facing surfaces 506, and a third gap region 528 disposed between the third set of opposed facing surfaces 508. A fourth gap region 530 is formed by the shape of a connecting portion 530 and provides a space for the displacement of the connecting portion 530, as described above.

In this embodiment, a dampening material 532 is disposed in two gap regions and provides dampening in both the upper and lower directions. In this embodiment, the dampening material is provided in the second and third gap regions 526, 528. Unlike the dampening material in FIG. 6C where the dampening material is a single mass extending in the second and third gap regions, the dampening material 532 is divided into individual elements 532, 534, with each element being disposed in a different gap region. In addition, unlike the dampening material in FIG. 6C where the dampening material fills the second and third gap regions, the dampening material 532 in FIG. 9A fills only a part of the height of the second and third gap regions 526, 528.

Because the dampening material fills only a part of the height of the gap regions 526, 528, the level of resistance to displacement is small or substantially linear for the first half of the motion range where the stop surfaces are not encountering resistance from the dampening material. When the stop surfaces eventually come into contact with the dampening material in the gap regions, the dampening material provides increasing or non-linear resistance as it compresses between the sets of mechanical stop surfaces. Accordingly, a curve showing the dampening resistance to motion distance in the embodiment of FIG. 9A may have a relatively linear resistance before the opposed facing surfaces of any set of mechanical stop surfaces contacts the dampening material, and then a relatively exponential resistance as the dampening material is compressed.

Such a system may be referred to as a "soft stop," as it does not have the same abrupt end of stop obtained when opposing mechanical stop surfaces engage without a dampening member disposed therebetween.

Figure 9B:
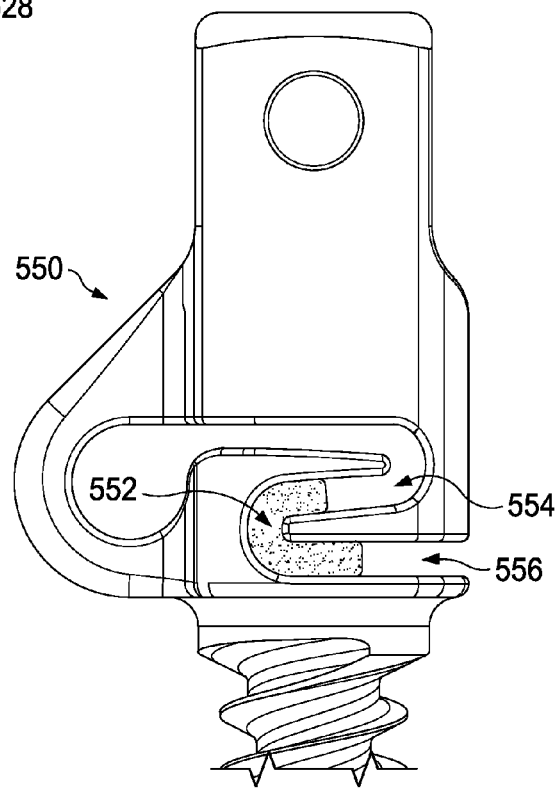
FIG. 9B is an illustration of another exemplary dynamic bone fastener for securing an elongated support structure in accordance with one or more aspects of the present disclosure.

FIG. 9B shows another embodiment of a bone fastener, referenced by the numeral 550. In many ways, the fastener 550 is similar to the fastener 500 in FIG. 9A. However, the dampening material is arranged in a slightly different fashion, where the dampening material fills only a part of each of the filled gap regions, but the dampening material is arranged to contact both the upper and lower mechanical stop surfaces of each gap region. In this example, the fastener 550 includes a dampening material 552 in a second gap region 554 and a third gap region 556. Accordingly, a resistance graph in this instance would not have the linear component discussed above because any motion would have some resistance applied by the dampening material.

Figure 9C:
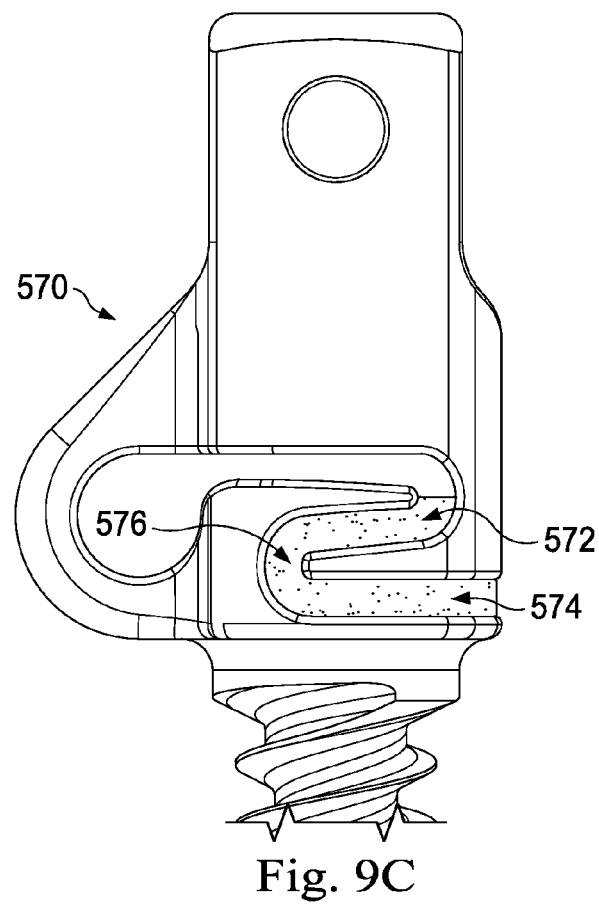
FIG. 9C is an illustration of another exemplary dynamic bone fastener for securing an elongated support structure in accordance with one or more aspects of the present disclosure.

FIG. 9C shows another embodiment of a bone fastener, referenced by the numeral 570. In many ways, the fastener 570 is similar to the fastener 500 in FIG. 9A. The fastener 570 includes a second gap region 572 and a third gap region 574 with a dampening material 576 disposed in the second and third gap regions 572, 576. The dampening material 576 is disposed in a manner similar in many ways to the dampening material in FIG. 6C. However, the dampening material 576 in FIG. 9C is a porous dampening material. In some examples, the porosity is in the range of 1% to 75%, and preferably 5% to 50%. This may include void volumes in a range of 1% to 75%, and preferably 5% to 50%. The porosity can be established to provide a desired level of dampening. In some embodiments, the porosity varies from gap region to gap region.

Figure 10A:
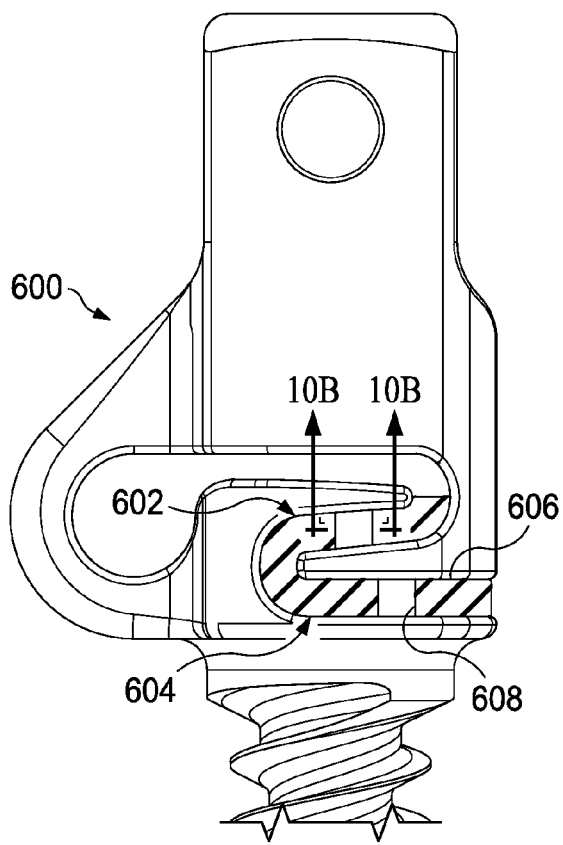
FIG. 10A is an illustration of another exemplary dynamic bone fastener for securing an elongated support structure in accordance with one or more aspects of the present disclosure.
Figure 10B:
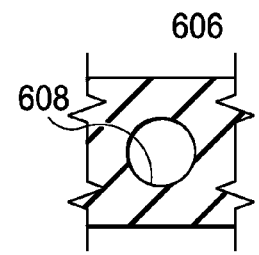
FIG. 10B is an illustration of another exemplary dynamic bone fastener for securing an elongated support structure in accordance with one or more aspects of the present disclosure.

FIG. 10A shows another embodiment of a bone fastener, referenced by the numeral 600. In many ways, the fastener 600 is similar to the fastener 500 in FIG. 9A. The fastener 600 includes a second gap region 602 and a third gap region 604 with a dampening material 606 disposed in the second and third gap regions 602, 604. The dampening material 606 is disposed in a manner similar in many ways to the dampening material in FIG. 9C. In FIG. 10A, the dampening material 606 is shown in cross-section to reveal a cavity 608 in the dampening material in each gap region 602, 604. The cavity 608 may be referred to as a macro-pore that affects the compressibility of the dampening material. FIG. 10B shows a top view of the dampening material 606 from either the first or second gap region 602, 604. As is apparent from FIG. 10B, the cavity 608 is centrally disposed in the dampening material. In the example shown, the cavity is round. However, the cavity may be formed of any shape and disposed at any location. For example, the cavity 608 may be square, rectangular, may be conical in cross-section or have other shapes. In addition, the cavity 608 may be disposed closer to one end than the other, may be oval shaped, or may be otherwise off-center. In one example, the cavity extends from one end of the fastening material, leaving the dampening material in a horse-shoe or U-shape. In other examples, the cavity extends from one end to the other, effectively splitting the dampening material into two sides.

In some examples, the dampening material 606 compresses in part by elastically collapsing into the cavity 608. As the cavity fills, the resistance to motion may be at a first level, and when the cavity fills with displaced dampening material, the resistance to motion may be at a second different level.

The dampening material 606 in FIGS. 10A and 10B, as well as all other embodiments herein, may extend to the edges of the gap regions. In so doing, the dampening material 606 may form a barrier to tissue ingrowth into the gap in the bone fasteners. Tissue ingrowth may adversely affect the reliability of the mechanical stops over time, affecting the range of motion obtainable by the bone fasteners. In the embodiment of FIGS. 10A and 10B, the cavity 608 may be sized large in order to provide minimal dampening to motion, but to provide a barrier to tissue ingrowth.

In any of the examples including dampening materials disclosed herein, the dampening material may occupy part or all of the gaps to modulate the resistance to motions. Depending on the embodiments, the dampening material may be not as wide as the gap, may not be a long as the gap, may not be as high as the gap (touching only one surface in neutral position), may have the same size and shape as the gap but may have through holes, ports, or cavities, or may have various levels of porosity.

Figure 11:
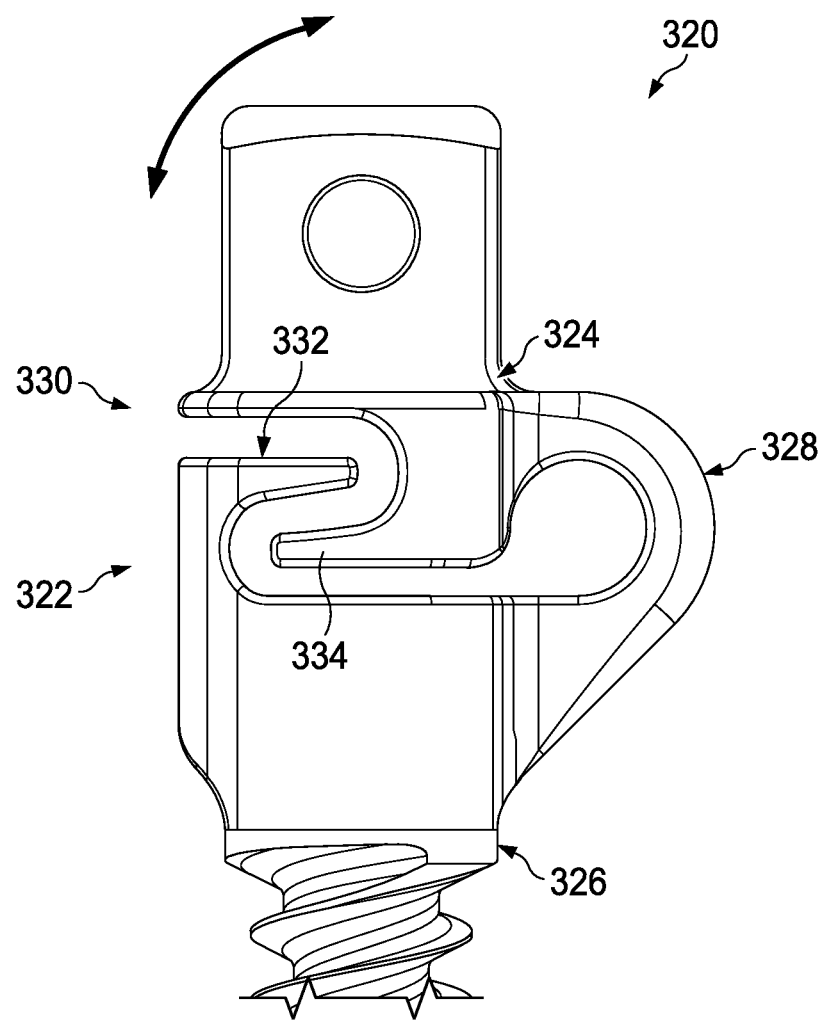
FIG. 11 is an illustration of another exemplary dynamic bone fastener for securing an elongated support structure in accordance with one or more aspects of the present disclosure.

FIG. 11 shows another embodiment of a bone fastener, referenced herein by the reference numeral 320. The fastener 320 is configured differently than the fasteners described above. Like the bone fastener 100 discussed above, the bone fastener 320 has a flexible portion 322 that includes an upper portion 324, a lower portion 326, a connecting portion 328, and a motion limiter portion 330. The motion limiter portion 330 limits the range of motion or articulation obtainable by the flexible portion 322 in both the upper and lower directions.

Here, the motion limiter portion 330 includes an inwardly projecting tab 332 and a catch 334 that cooperate to limit the range of possible motion. Each of the tab 332 and the catch 334 include mechanical stop surfaces that limit the range of motion of the dynamic bone fastener 320. Unlike the example shown in FIG. 1, in this exemplary embodiment, the tab 332 extends inwardly from an arm 336 connected to the lower portion 326 instead of the upper portion, as shown in FIG. 1. The catch 334 extends from the upper portion 324.

FIGS. 12-14 show a plurality of bone fasteners 340, 342, 344, respectively with different arrangements of the flexible connecting portions, but each having similar motion limiter portions.

Figure 15:
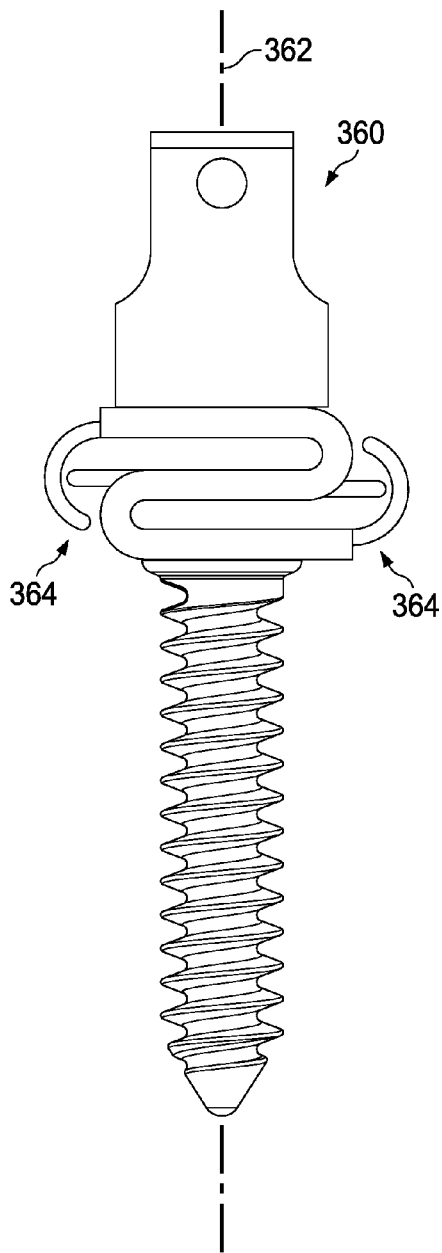
FIGS. 15 and 16 are illustrations of other exemplary dynamic bone fasteners for securing an elongated support structure in accordance with one or more aspects of the present disclosure.
Figure 16:
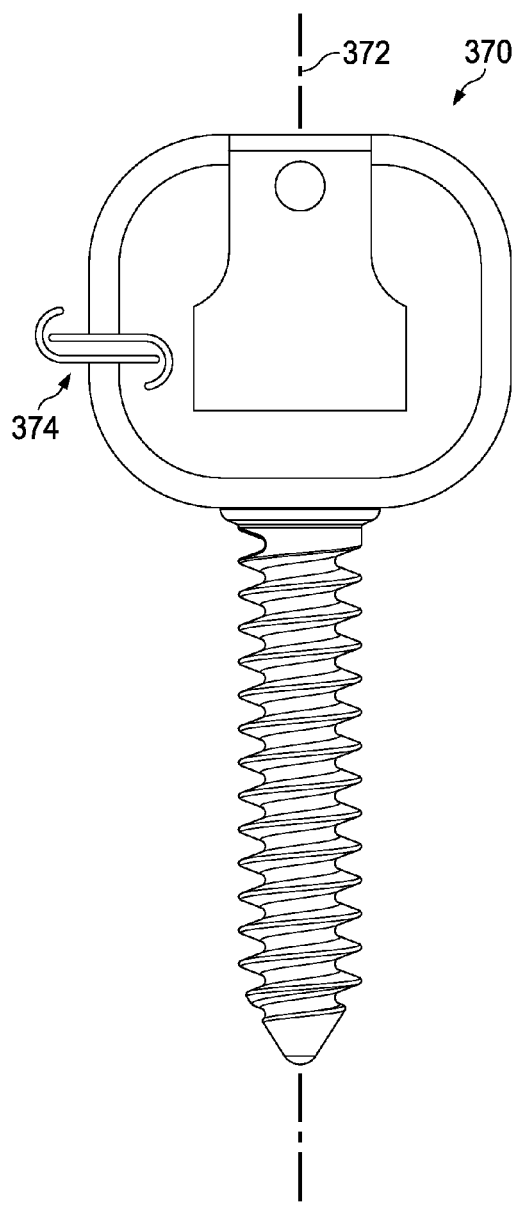

FIGS. 15 and 16 show different bone fastener embodiments where the motion limiter portion of each bone fastener is offset to the side of the longitudinal axis. FIG. 15 shows a bone fastener 360 having a longitudinal axis 362 and a motion limiter portion 364 including portions arranged in part along sides of the bone fastener. The motion limiter portions 364 have sets of opposed facing surfaces that cooperate to limit the range of movement in both the upward and downward directions. FIG. 16 shows a bone fastener 370 having a longitudinal axis 372 and a motion limiter portion 374 having sets of opposed facing surfaces that cooperate to limit the range of movement in both the upward and downward directions.

Figure 17:
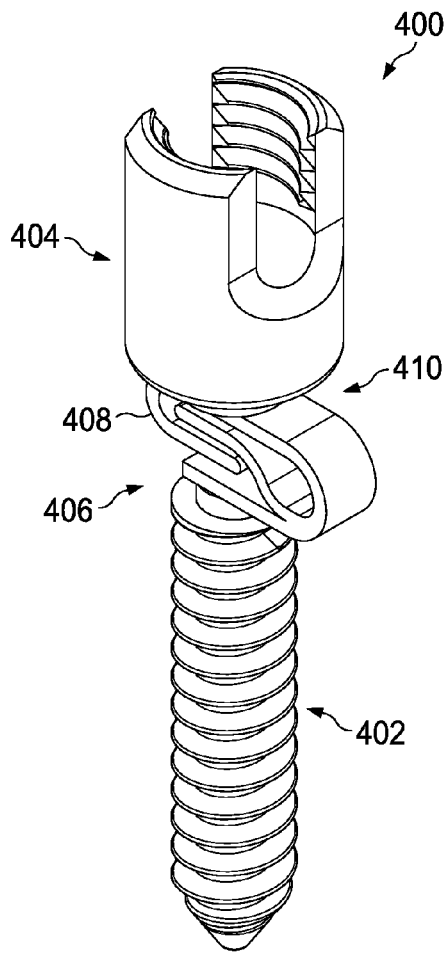
FIGS. 17 and 18 are illustrations of other exemplary dynamic bone fasteners for securing an elongated support structure in accordance with one or more aspects of the present disclosure.
Figure 18:
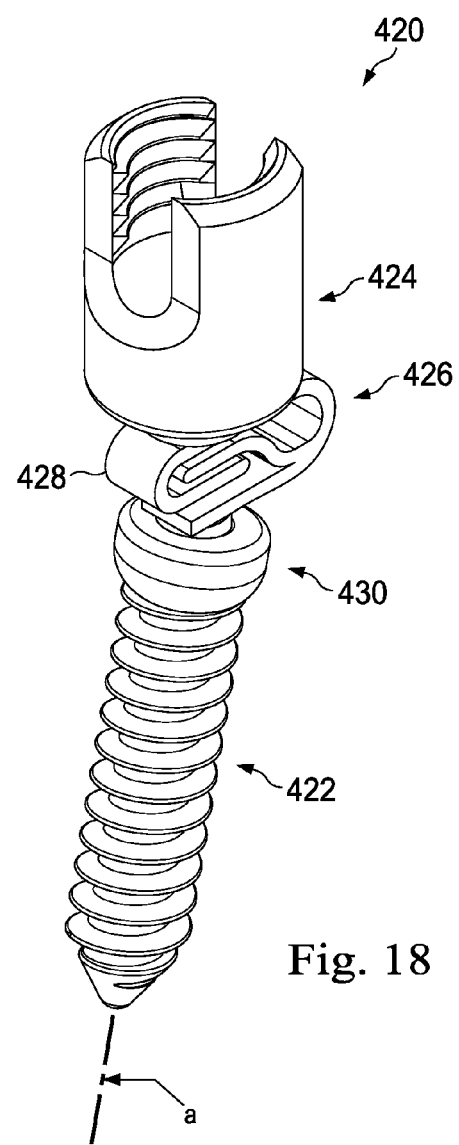

FIGS. 17 and 18 are examples of multi-axial fasteners including the flexible portions disclosed herein. FIG. 17 discloses a bone fastener 400 that includes a fixation portion 402, a connection portion 404, and a flexible portion 406. The flexible portion 406 includes a motion limiter portion 408 and is disposed between the attachment portion 402 and the connection portion 404. An articulation mechanism 410 (shown as a ball joint in FIG. 17) provides the multi-axial capability and is disposed between the flexible portion 406 and the connection portion 404.

FIG. 18 discloses a bone fastener 420 that includes a fixation portion 422, a connection portion 424, and a flexible portion 426. The flexible portion 426 includes a motion limiter portion 428 between the attachment portion 422 and the connection portion 424. In this embodiment however, an articulation mechanism 430 providing the multi-axial capability is disposed between the flexible portion 426 and the attachment portion 422.

Figure 19:
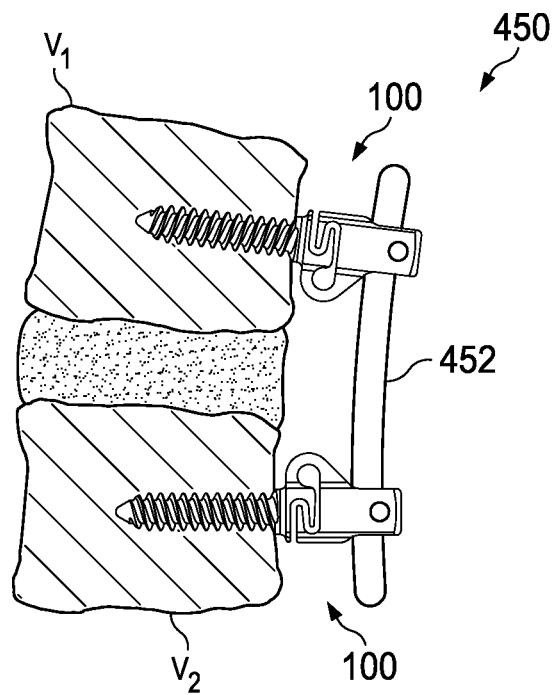
FIG. 19 is an illustration of exemplary dynamic bone fasteners securing an elongated support structure in accordance with one or more aspects of the present disclosure.

FIG. 19 shows an example of a bone fastener system 450 formed of bone fasteners 100 and an elongated support structure 452 extending therebetween. As shown, the system 450 includes two bone fasteners 100 each implanted in a vertebral body V1, V2, with the elongated support structure 452 extending therebetween. The bone fasteners 100, with their dynamic motion capabilities, better distribute loading and reduce stresses on the bone structure.

FIG. 19 shows one example of how the bone fasteners may be arranged when connected to an elongated support structure. As shown the connecting portions of each bone fastener are facing the opposing bone fastener.

Conventional systems using conventional rigid fasteners may have bone screws that loosen over time within the vertebral structure due to cyclic loading from patient movement. This may eventually cause some degree of loading resulting in a wind-shield wiper effect, where the distal end of the bone screw pivots slightly relative to the bone sidewall. However the present dynamic fasteners 100 may help reduce the stresses at the bone-fastener interface, reducing the potential for fastener loosening.

Figure 20:
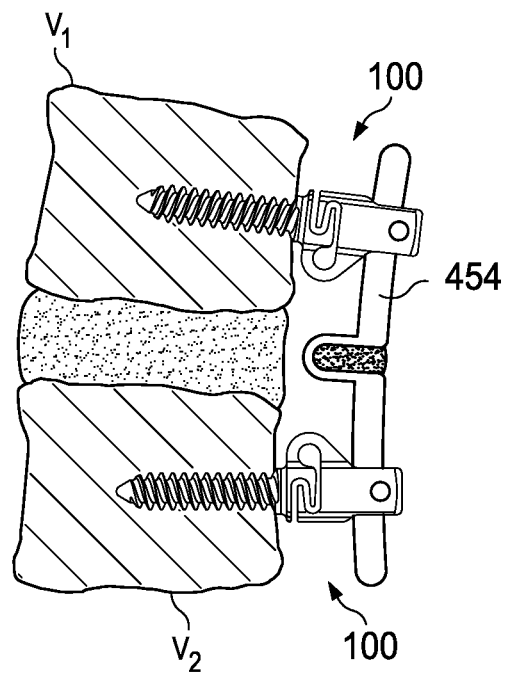
FIG. 20 is an illustration of exemplary dynamic bone fasteners securing an elongated support structure in accordance with one or more aspects of the present disclosure.

FIG. 20 shows another example of a bone fastener system 450. This system however different from that of FIG. 19 because it uses a flexible or dynamic rod 454. One example of a rod that may be used in the bone fastener system is found in U.S. patent application Ser. No. 12/394,362, filed Feb. 27, 2009, titled Vertebral Rod System and Method of Use, and incorporated herein by reference. In some systems, the bone fasteners 100 may face away from each other as shown in FIG. 19. In other embodiments however, the bone fasteners 100 may face toward each other. In yet other embodiments, the bone fasteners may face in the same direction.

Figure 21:
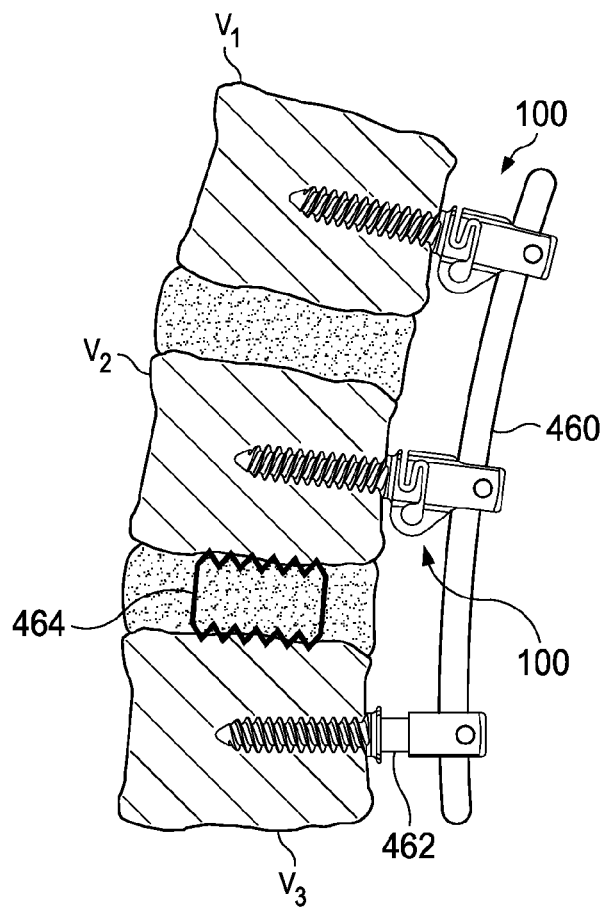
FIGS. 21 and 22 are illustrations of other exemplary dynamic bone fasteners securing an elongated support structure in accordance with one or more aspects of the present disclosure.

FIG. 21 shows an example of a bone fastener system 450 formed of bone fasteners and an elongated support structure 460. This embodiment includes two dynamic bone fasteners 100 as described herein, and includes one conventional rigid bone fastener 462, each driven into adjacent vertebral bodies of a vertebral column. The elongated support structure 460 connects the three bone fasteners 100, 462 to provide stabilizing support to two levels of the vertebral column.

In addition, this embodiment shows the system 450 cooperating with a fusion cage/graft 464 to fuse the second level of the vertebral column. Accordingly, this embodiment provides dynamic stabilization at level 1 and provides fusion stabilization at level 2. Other embodiments do not employ the fusion cage, such that both levels 1 and 2 are dynamically stabilized. Yet other embodiments use a fusion cage or a prosthetic disc at level 1. It should be noted that the same system can be extended to three or more levels for stabilization using the dynamic bone fasteners for either fusion or motion preserving.

Some embodiments of the system 450 use only a single dynamic bone fastener 100 and use a plurality of conventional bone screws, such as mono-axial or multi-axial bone screws. In embodiments having a fusion cage, these conventional bone screws may be anchored in the vertebral bodies adjacent the fusion cage, and the dynamic bone fastener may be anchored at a location to provide additional dynamic support.

Figure 22:
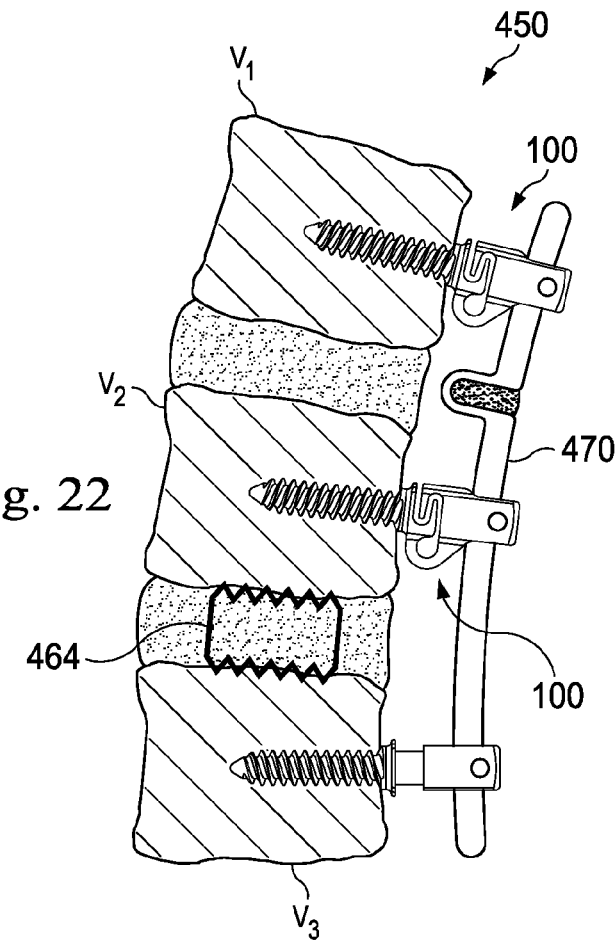

FIG. 22 shows an example of a bone fastener system 450 formed of bone fasteners as described in FIG. 21 and an elongated support structure 470. In this embodiment, the elongated support structure 470 is a posterior transition device (PTD) rod having a lower rigid section for fusion purposes and an upper flexible section for dynamic stabilization. A PTD rod is used to stabilize a first fusion level and a second dynamic level. The dynamic nature of the upper level is attributed to the flexible section of the flexible elongated support structure 470 and the flexible portions of the dynamic bone fasteners 100. In some embodiments, a disc prosthesis of nucleus implant may support the anterior column at the dynamic upper level.

It is worth noting that any of the fastener embodiments described herein can be modified and optimized to fit various applications or purposes (e.g. more rigid constructs for spinal fusion, more compliant constructs for dynamic stabilization, "top-off" constructs with various combinations of more rigid and more compliant levels, etc., osteoporotic bones that need more load-sharing screws, etc. In addition, it is contemplated that many variations in geometry and size of the flexible sections and the stopping features may be provided, and are intended to fall within the scope of this disclosure.

Further, it should be noted that the features described in any one embodiment in this disclosure may be used with any other embodiment. For example, any fastener may include a dampening material in a gap or in gaps in the flexible portion. As another example, any fastener in this disclosure may be used in the systems disclosed in FIGS. 19-22. It is contemplated that other features of one embodiment can be used in other embodiments, and the above referenced devices are examples only.

In some examples, the flexible portions of the fastening members are formed of a material that is treated to increase fatigue resistance and durability. For example, the flexible portions may be shot-peened, laser-peened, heat treated, or otherwise treated to increase the life of the fastener.

The components of the bone fastener 100 and elongated support structure employed therewith, are fabricated from materials suitable for medical applications, including metals, polymers, ceramics, biocompatible materials and/or their composites, depending on the particular application and/or preference of a medical practitioner. For example, the bone fastener 100 and/or an elongated support structure, such as a vertebral rod of a vertebral rod system can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO4 composites, ceramics and composites thereof such as calcium phosphate (e.g., SKELITE™), rigid polymers including polyphenylene, polyamide, polyimide, polyetherimide, polyethylene, polyurethanes of any durometer, epoxy and silicone. Different components may have alternative material composites to achieve various desired characteristics such as strength, rigidity, elasticity, compliance, biomechanical performance, durability and radiolucency or imaging preference. The components may also be fabricated from a heterogeneous material such as a combination of two or more of the above-described materials.

The bone fasteners disclosed herein can be formed of two or more materials, with different portions being formed of different materials. In one example, the anchoring portion is formed of a titanium material, the connecting portion is formed of a cobalt chromium material, and the flexible portion is formed of a PEEK material. In another example, the anchoring and connecting portions are formed of titanium and the flexible portion is formed of Nitinol. In one embodiment, different portions of the bone fasteners can be fabricated from carbon-reinforced PEEK and an intermediate section can be fabricated from PEEK. In one embodiment, the first and second sections are fabricated from PEEK and the intermediate section is fabricated from carbon-reinforced PEEK. In one embodiment, the fixation portion is fabricated from a first material, such as those described above, and the flexible portion is fabricated from a second material such as, for example, Nitinol, PEEK, carbon-PEEK, a titanium alloy and/or a cobalt-chrome alloy. In one embodiment, alternate materials may be employed in a radial direction of bone fastener 100 such that stiff materials such as metals or other composites are used in a core of the fastener sections and an outer sheet of lower modulus polymeric material is used in the outer radial portion of the fastener portions, or vice versa.

As a further example, the dampening material of the bone fasteners herein may be fabricated from materials such as silicone, polyurethane, silicone-polyurethane copolymers, polymeric rubbers, polyolefin rubbers, hydrogels, semi-rigid and rigid materials, and biocompatible materials such as elastomers, rubbers, thermoplastic elastomers, thermoset elastomers, elastomeric composites and plastics. In some examples, the durometer hardness of material used for the dampening material is in the range of 30 Shore A to 90 Shore D, preferably between 50 Shore A to 55 Shore D. It is envisioned that the components of the vertebral rod system can be manufactured via various methods. For example, bone fastener 30 can be manufactured and assembled via injection-molding, insert-molding, overmolding, compression molding, transfer molding, co-extrusion, pultrusion, dip-coating, spray-coating, powder-coating, porous-coating, machining, milling from a solid stock material, and their combinations. One skilled in the art, however, will realize that such materials and fabrication methods suitable for assembly and manufacture, in accordance with the present disclosure, would be appropriate.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

What is claimed is:

1. A bone fastener having a longitudinal axis and being configured to penetrate into boney tissue and connect with a rod, comprising:
    a fixation portion comprising a threaded shaft configured to interface with the boney tissue;
    a connection portion comprising a concave cavity extending transverse to the longitudinal axis configured to interface with the rod;
    a flexible portion disposed between the fixation portion and the connection portion such that the fixation portion and the flexible portion are coaxial, the flexible portion being configured to permit flexure of the connection portion relative to the fixation portion, the flexible portion having a first set of opposed facing surfaces that mechanically limit a range of flexure in a first direction, and having a second set of opposed facing surfaces that mechanically limit the range of flexure in a second direction, wherein the first and second sets of opposed facing surfaces are transverse to the longitudinal axis, and the flexible portion has a maximum width extending transverse to the longitudinal axis that is greater than a maximum width of the fixation portion extending transverse to the longitudinal axis and a maximum width of the connection portion extending transverse to the longitudinal axis; and
    an arcuate connecting portion extending between upper and lower portions of the flexible portion, the upper portion merging with the connection portion such that the upper portion extends away from the connection portion in a direction that faces away from the longitudinal axis and the lower portion merging with the fixation portion such that the lower portion extends away from the fixation portion in a direction that faces away from the longitudinal axis.

2. The bone fastener of claim 1, wherein:
    the first set of opposed facing surfaces comprises mechanical stop surfaces that provide a first stop limit; and
    the second set of opposed facing surfaces comprises mechanical stop surfaces that provide a second stop limit, and
    the range of flexure being limited by mechanical interference of the mechanical stop surfaces.

3. The bone fastener of claim 1, further comprising a dampening material disposed between the first set of opposed facing surfaces and disposed between the second set of opposed facing surfaces.

4. The bone fastener of claim 3, further wherein the dampening material is disposed to fill only a portion of an area between the first set of opposed facing surfaces and to fill only a portion of an area between the second set of opposed facing surfaces.

5. The bone fastener of claim 1, wherein the flexible portion comprises an upper portion, a lower portion, a connecting portion, and a gap disposed between the upper and lower portions, the connecting portion being configured to bias the flexible portion to a neutral position.

6. The bone fastener of claim 5, wherein:
    the first set of opposed facing surfaces comprises mechanical stop surfaces that provide a first stop limit;
    the second set of opposed facing surfaces comprises mechanical stop surfaces that provide a second stop limit, and
    when the flexible portion is in the neutral position, a distance between the mechanical stop surfaces of the first set of opposed facing surfaces is different than a distance between the mechanical stop surfaces of the second set of opposed facing surfaces.

7. The bone fastener of claim 1, wherein the first set of opposed facing surfaces comprises an upper mechanical stop surface and a lower mechanical stop surface, one being disposed above the other.

8. The bone fastener of claim 7, further comprising a dampening material disposed between the upper mechanical stop surface and the lower mechanical stop surface.

9. The bone fastener of claim 8, wherein the flexible portion includes an elastically deformable portion, and wherein the dampening member is disposed adjacent the elastically deformable portion to affect the dampening.

10. The bone fastener of claim 1, wherein the bone fastener further comprises a pivoting mechanism allowing the fixation portion to pivot relative to the connection portion, such that the bone fastener is a multi-axial bone fastener.

11. The bone fastener of claim 1, wherein a first distance between the first set of opposed facing surfaces forms a first gap region, and wherein a second distance between the second set of opposed facing surfaces forms a second gap region.

12. The bone fastener of claim 11, wherein the first distance is greater than the second distance.

13. The bone fastener of claim 11, wherein the flexible portion further comprises a third set of opposed facing surfaces that mechanically limits the range of flexure in the first direction, and wherein a distance between the third set of opposed facing surfaces forms a third gap region.

14. The bone fastener of claim 13, further comprising a dampening material disposed in the first gap region and in the second gap region.

15. The bone fastener of claim 1, wherein the connection portion comprises a pair of spaced apart arms that define the cavity, the cavity extending through an uppermost surface of the connection portion such that the cavity is U-shaped and configured to have the rod top-loaded therein.

16. A bone fastener having a longitudinal axis and being configured to penetrate into boney tissue and connect with a rod, comprising:

a fixation portion comprising a threaded shaft configured to interface with the boney tissue;
a connection portion comprising a concave cavity extending transverse to the longitudinal axis configured to interface with the rod;
a flexible portion disposed between the fixation portion and the connection portion such that the fixation portion and the flexible portion are coaxial, the flexible portion being configured to permit flexure of the connection portion relative to the fixation portion, the flexible portion comprising:
an upper portion merging with the connection portion and extending away from the connection portion in a direction that faces away from the longitudinal axis,
a lower portion merging with the fixation portion and extending away from the fixation portion, and
a motion limiter portion comprising:
a first set of opposed facing surfaces that mechanically limits a range of flexure in a first direction, wherein a first distance between the first set of opposed facing surfaces forms a first gap region, and
a second set of opposed facing surfaces that mechanically limits the range of flexure in a second direction, wherein a second distance between the second set of opposed facing surfaces forms a second gap region, wherein the first and second sets of opposed facing surfaces are transverse to the longitudinal axis and the flexible portion has a maximum width extending transverse to the longitudinal axis that is greater than a maximum width of the fixation portion extending transverse to the longitudinal axis and a maximum width of the connection portion extending transverse to the longitudinal axis; and
a connecting portion connecting the upper portion to the lower portion, the connecting portion being configured to flex to displace the upper portion relative to the lower portion.

17. The bone fastener of claim 16, further comprising a dampening material disposed between the first set of opposed facing surfaces and disposed between the second set of opposed facing surfaces.

18. The bone fastener of claim 16, wherein:
the first set of opposed facing surfaces comprises an upper mechanical stop surface and a lower mechanical stop surface, one being disposed above the other; and
the first set of opposed facing surfaces is positioned vertically above the second set of opposed facing surfaces.

19. A system for stabilization of boney structure comprising:
a rod;
at least two bone fasteners configured to penetrate into boney tissue and connect with the rod, each bone fastener comprising:
a fixation portion defining a longitudinal axis and comprising a threaded shaft configured to interface with the boney tissue;
a connection portion comprising a concave cavity extending transverse to the longitudinal axis configured to interface with the rod;
a flexible portion disposed between the fixation portion and the connection portion such that the fixation portion and the flexible portion are coaxial, the flexible portion being configured to permit flexure of the connection portion relative to the fixation portion, the flexible portion having a first set of opposed facing surfaces that mechanically limits a range of flexure in a first direction, and having a second set of opposed facing surfaces that mechanically limits the range of flexure in a second direction, wherein the first and second sets of opposed facing surfaces are transverse to the longitudinal axis and the flexible portion has a maximum width extending transverse to the longitudinal axis that is greater than a maximum width of the fixation portion extending transverse to the longitudinal axis and a maximum width of the connection portion extending transverse to the longitudinal axis; and
an arcuate connecting portion extending between upper and lower portions of the flexible portion, the upper portion merging with the connection portion such that the upper portion extends away from the connection portion in a direction that faces away from the longitudinal axis and the lower portion merging with the fixation portion such that the lower portion extends away from the fixation portion in a direction that faces away from the longitudinal axis.

20. The system of claim 19, wherein:
the first set of opposed facing surfaces comprises an upper mechanical stop surface and a lower mechanical stop surface, one being disposed above the other; and
the first set of opposed facing surfaces is positioned vertically above the second set of opposed facing surfaces.

\* \* \* \* \*